(12) United States Patent
Jaecker et al.

(10) Patent No.: US 12,396,751 B2
(45) Date of Patent: *Aug. 26, 2025

(54) NESTED CANNULA SYSTEM

(71) Applicant: Acumed LLC, Hillsboro, OR (US)

(72) Inventors: Devan Jaecker, Beaverton, OR (US); Dustin Cluff, St. Helens, OR (US); Stanley J. Langford, Hillsboro, OR (US); Andrew W. Seykora, Portland, OR (US)

(73) Assignee: Acumed LLC, Hillsboro, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/531,382

(22) Filed: Dec. 6, 2023

(65) Prior Publication Data

US 2024/0099742 A1    Mar. 28, 2024

Related U.S. Application Data

(63) Continuation of application No. 17/153,391, filed on Jan. 20, 2021, now Pat. No. 11,857,217.

(60) Provisional application No. 62/964,450, filed on Jan. 22, 2020.

(51) Int. Cl.
A61B 17/34    (2006.01)

(52) U.S. Cl.
CPC .... *A61B 17/3439* (2013.01); *A61B 2017/347* (2013.01)

(58) Field of Classification Search
CPC ............... A61B 17/3439; A61B 2017/347
See application file for complete search history.

(56) References Cited

U.S. PATENT DOCUMENTS

| 2005/0080443 | A1 | 4/2005 | Fallin et al. |
| 2006/0004398 | A1 | 1/2006 | Binder, Jr. et al. |
| 2007/0255305 | A1 | 11/2007 | McMichael et al. |
| 2009/0149857 | A1 | 6/2009 | Culbert et al. |

*Primary Examiner* — Ashley L Fishback
(74) *Attorney, Agent, or Firm* — Knobbe, Martens, Olson & Bear, LLP

(57) ABSTRACT

The present disclosure provides for an interlocking cannula system that includes a handle and a set of cannulas. The set of cannulas includes a sequence of smaller to larger cannulas constructed such that the smaller cannulas may be nested within larger cannulas. Each cannula in the set of cannulas includes a respective locking mechanism configured such that each cannula may be interlocked with each of the other cannulas in the set. The handle is constructed such that each cannula in the set may interlock with the handle by the respective locking mechanism of the cannula. In some instances, the respective locking mechanisms are constructed to enable an ordered release of the cannulas.

19 Claims, 13 Drawing Sheets

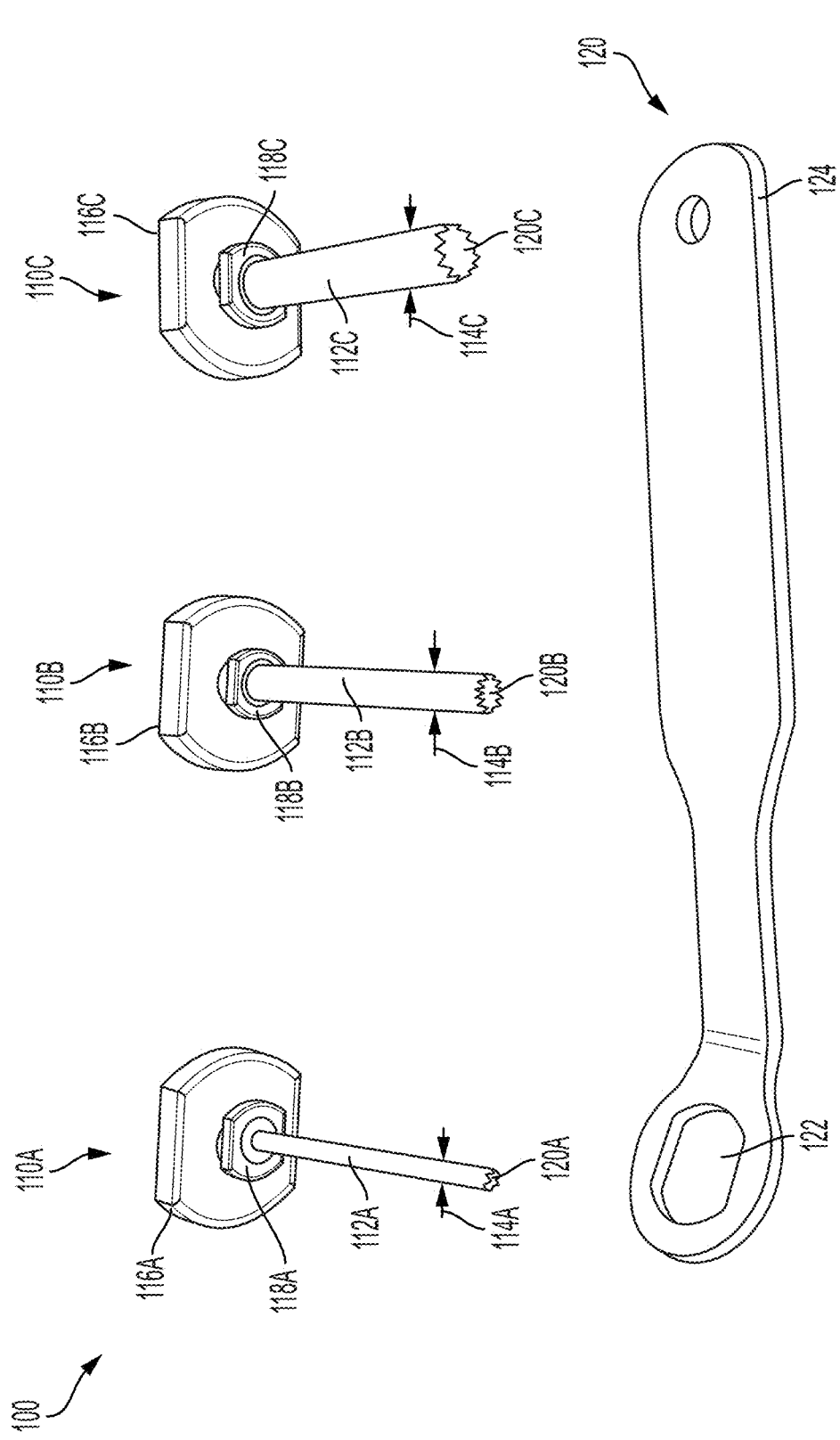

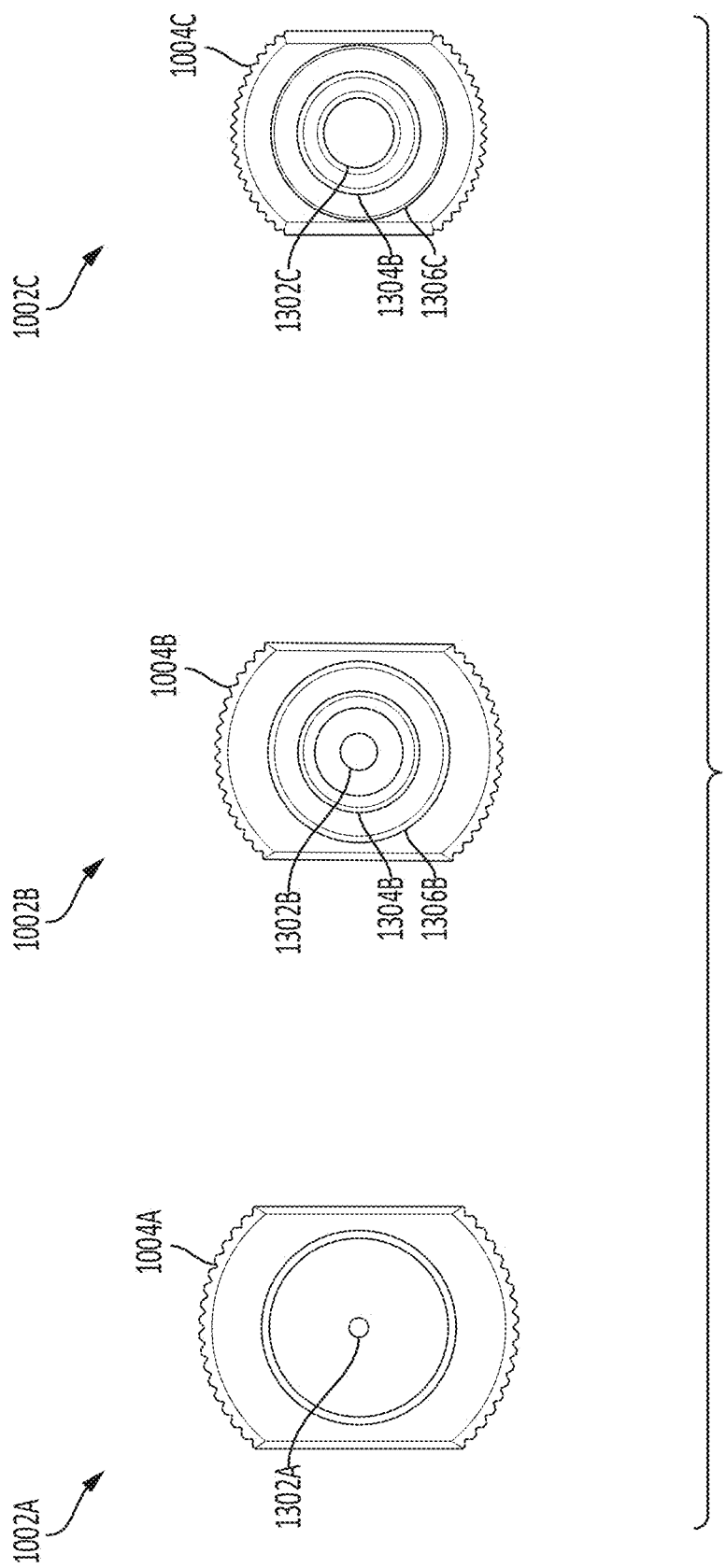

NESTED CANNULA SYSTEM

PRIORITY CLAIM

The present application is a continuation of U.S. patent application Ser. No. 17/153,391 filed on Jan. 20, 2021, which claims priority to and the benefit of U.S. Provisional Application 62/964,450 filed Jan. 22, 2020, which are each incorporated herein by reference in their entirety for all purposes.

BACKGROUND

Various surgical procedures often require surgeons to access many different areas of a patient's body. In some instances, however, human anatomy prevents a surgeon from direct access to the subject area of a procedure. For instance, bone or soft tissue may be blocking the surgeon's access, and thus the surgeon must drill a hole through the bone or make an incision in the soft tissue to access the subject area. To maintain access to the subject area, a surgeon may insert a cannula. A cannula includes a hollow tube and thus enables the surgeon to insert various surgical instruments through the hollow tube to access the subject area for the surgical procedure. The cannula may also protect the patient's soft tissue surrounding the cannula from damage by the surgical instruments.

A surgical procedure often requires a surgeon to use multiple different surgical instruments, which are often different sizes. Thus, when a surgeon uses a cannula, the cannula must have a large enough passageway such that the largest instrument (e.g., implant) for the procedure may fit through the cannula. For some instruments, however, if the cannula passageway is too large as compared to the instrument, it may be more difficult for the surgeon to finely control the instrument. Thus, a surgeon may preferably need different sized cannulas for different instruments.

One way for a surgeon to be provided different-sized cannulas is for the surgeon to switch out a cannula each time the surgeon needs a different size. This method, however, provides the surgeon with extra labors with how to perform a procedure. For instance, in some instances, it may increase surgical procedure time and the potential for soft tissue irritation/damage as changing the size of the cannula necessitates removing the cannula from the surgical site and inserting the desired cannula into the site. Additionally, if the incision was not made large enough to fit the largest required cannula, the surgeon may have to increase the size of the incision mid-surgery, adding to the surgical time. In another instance, an incision made for a large cannula will not be suitable for a small cannula, and thus once a surgeon makes an incision for a large cannula, the surgeon can no longer use a small cannula unless the surgeon makes a new incision at a different location. Accordingly, the surgeon is limited to using surgical instruments in increasing size of surgical instrument, which is not desirable. It is additionally not desirable for a surgeon to make multiple incisions for different-sized cannulas as this increases a patient's healing time.

Another way for a surgeon to be provided different-sized cannulas is a nested cannula system. A nested cannula system includes multiple different-sized cannulas that may nest within one another in a telescoping fashion. Thus, when a surgeon needs a smaller cannula, the surgeon may insert the smaller cannula within the larger cannula that is already within the patient, rather than switching the cannulas or making a new incision. Conventional nested cannula systems, however, may include an attached handle on a single cannula size, thus necessitating that a surgeon always use the cannula size with the attached handle. This provides the surgeon with limited flexibility, and in some instances, may require the surgeon to use a larger cannula than needed, which requires the surgeon to make a larger incision (or drill a larger bone hole) than would be required with a smaller cannula. The larger incision or bone hole results in a longer recovery time for the patient.

Some conventional nested cannula systems may include attached handles on multiple cannula sizes. The additional handles in such systems, however, generate additional weight that may place additional stress on a patient's soft tissue, bone, joint, etc. The additional handles also generate additional components that a surgeon must be mindful of and control when performing a procedure.

In addition, some conventional nested cannula systems may rely on the diametric fit between cannula sizes for maintaining concentricity between the smallest and largest cannulas. This reliance accordingly necessitates that a surgeon use all intermediate cannulas between two sizes, which also generates additional weight that may place additional stress on a patient's soft tissue, bone, joint, etc. Some conventional nested cannula systems additionally rely on friction between adjacently-sized cannulas to retain one cannula with another. This reliance also necessitates that a surgeon use all intermediate cannulas between two sizes. Additionally, friction-based retention may disengage and/or allow rotation between cannulas when forces are applied through a surgical instrument to the underlying bone in contact with the outermost cannula.

Accordingly, a need exists for a nested cannula system that provides surgeons with greater flexibility and reduces patient recovery times as compared to conventional nested cannula systems.

SUMMARY

The present disclosure provides new and innovative interlocking nested cannula systems and methods for surgical procedures. Each cannula in the provided system may be used individually with a handle, or may be interlocked with any other cannula in the system. In this way, the provided nested cannula system enables a surgeon to use the smallest cannula that is needed for a given procedure and to skip unneeded cannula sizes when switching from one size to another.

In an example, a system includes a handle and a plurality of cannulas. The plurality of cannulas include a sequence of smaller to larger cannulas that are configured such that smaller cannulas may be nested within larger cannulas. Each cannula of the plurality of cannulas includes a respective locking mechanism configured such that each cannula may be interlocked with each of the other cannulas of the plurality of cannulas. Additionally, the handle is configured such that each cannula of the plurality of cannulas may interlock with the handle by the respective locking mechanism of the cannula.

In another example, a method includes inserting into a patient at least a portion of a set of nested cannulas including a first cannula, a second cannula, and a third cannula. The second cannula is nested within, and interlocked with, the first cannula, and the third cannula is nested within, and interlocked with, the second cannula. Either the third cannula is removed from within the second cannula while the second cannula remains nested within, and interlocked with, the first cannula or the second cannula is removed from within the first cannula while the third cannula remains nested within, and interlocked with, the second cannula.

Additional features and advantages of the disclosed method and apparatus are described in, and will be apparent from, the following Detailed Description and the Figures. The features and advantages described herein are not all-inclusive and, in particular, many additional features and advantages will be apparent to one of ordinary skill in the art in view of the figures and description. Moreover, it should be noted that the language used in the specification has been principally selected for readability and instructional purposes, and not to limit the scope of the inventive subject matter.

BRIEF DESCRIPTION OF THE DRAWINGS

FIG. 1 illustrates a perspective view of an example cannula system, according to an aspect of the present disclosure.

FIG. 13 illustrates a top view of the cannulas of FIG. 10, according to an aspect of the present disclosure.

DETAILED DESCRIPTION

Figure 2A:
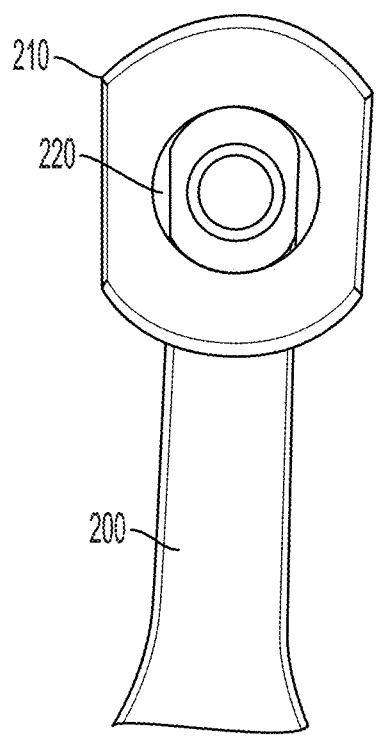
FIGS. 2A and 2B illustrate top views of an example engagement of a locking mechanism, according to an aspect of the present disclosure.

The present disclosure relates generally to cannulas for surgical procedures. More specifically, the present disclosure provides a nested cannula system in which each cannula in the system may be used individually with a handle, or may be interlocked with any other cannula in the system. When two cannulas are interlocked with one another, one cannula is nested within a second cannula. The handle is a separate handle component of the provided cannula system that may be used with each cannula individually. In this way, the presently disclosed nested cannula system enables a surgeon to use the smallest cannula that is needed for a given procedure, which results in smaller incisions or bone holes and faster patient recovery times. The presently disclosed nested cannula system additionally enables a surgeon to skip unneeded cannula sizes when switching from one size to another since each cannula may be used with any other cannula by way of respective locking mechanisms on each cannula. In this way, the provided cannula system can help place less stress on a patient's soft tissue, bone, joint, etc. by eliminating the need to use all intermediate cannulas as compared to typical nested cannula systems.

The respective locking mechanisms of the provided cannulas interlock two nested cannulas with one another. In at least some aspects, the respective locking mechanisms maintain concentricity between two nested cannulas. In some aspects, a respective locking mechanism may prevent rotation between two nested cannulas with respect to one another. In some aspects, the respective locking mechanisms may be constructed to enable an ordered release of nested and interlocked cannulas such that, for example, it is easier (e.g., requires less force) to disengage and remove a first cannula from a second cannula than it is to disengage and remove the second cannula from a third cannula. The ordered release can help a surgeon disengage and remove the first cannula without disengaging or removing the second and third cannulas, and in at least some instances, can help the surgeon do this with one hand to free up the surgeon's other hand during surgery.

FIG. 1 illustrates an example cannula system 100, according to an aspect of the present disclosure. In some aspects, the example cannula system 100 includes a handle 120 and three differently-sized cannulas 110A, 110B, and 110C. In other aspects, the cannula system 100 may include more than three differently-sized cannulas 110A, 110B, 110C. The cannula 110A includes a head 116A, and tube 112A with a diameter 114A. The cannula 110B similarly includes a head 116B, and a tube 112B with a diameter 114B. The cannula 110C similarly includes a head 116C, and a tube 112C with a diameter 114C.

The cannulas 110A, 110B, and 110C are sized in a sequence of smaller cannulas to larger cannulas. For instance, the cannula 110C is larger than the cannula 110B, which is larger than the cannula 110A. For example, the diameter 114C of the tube 112C is larger than the diameter 114B of the tube 112B, which is larger than the diameter 114A of the tube 112A. In aspects in which the cannula system 100 includes more than three cannulas 110A, 110B, 110C, the sequence may further include a cannula larger than the cannula 110C or a cannula smaller than the cannula 110A, and so forth.

In some aspects of the present disclosure, it may be only the respective tubes 112A, 112B, and 112C of each cannula 110A, 110B, 110C in the cannula system 100 that change in size. Stated differently, in such aspects only the diameters 114A, 114B, and 114C of the respective tubes 112A, 112B, and 112C change in size among the sequence of cannulas while the size of the respective heads 116A, 116B, and 116C remain the same. Each cannula 110A, 110B, 110C has a channel 120A, 120B, 120C that extends the length of the cannula 110A, 110B, 110C, through the respective heads 116A, 116B, 116C and respective tubes 112A, 112B, 112C, with an opening at each end. The difference in diameters 114A, 114B, 114C between the tubes 112A, 112B, 112C of the cannulas 110A, 110B, 110C enables the cannulas 110A, 110B, and 110C to be nested within one another. For example, the tube 112A of the cannula 110A may be placed within the channel 120B of the cannula 110B or the channel 120C of the cannula 110C, and the tube 112B of the cannula 110B may be placed within the channel 120C of the cannula 110C.

In various aspects of the present disclosure, the example handle 120 of the cannula system 100 includes a gripping portion 124 and an opening 122. In some aspects, the gripping portion 124 may have suitable shapes other than that illustrated and/or may include additional material for enhancing grip, such as rubber, on the outer surface. The opening 122 of the handle 120 is configured according to a locking mechanism of each cannula 110A, 110B, 110C in order to enable interlocking a respective cannula 110A, 110B, 110C with the handle 120. For example, in some aspects, such as the one illustrated, each locking mechanism is a twist lock mechanism such that a first cannula (e.g., the cannula 110A) is twisted or rotated relative to a second cannula (e.g., the cannula 110B) in order to lock the first and second cannulas. In such an example, the twist lock mechanism may include a male lock component and a female lock component or opening. The female lock opening allows the male lock component to pass through when the male lock component is in one orientation, but does not let it pass through when the male lock component is rotated relative to the female lock opening.

In an example, each cannula 110A, 110B, 110C includes a male lock component 118A, 118B, 118C that includes a cross-sectional shape with two straight sides and two curved sides. Each cannula 110A, 110B, 110C also includes a female lock component or opening (not illustrated), which will be described in more detail below. In various aspects, the example opening 122 of the handle 120 has the same corresponding cross-sectional shape as each male lock component 118A, 118B, and 118C. In such aspects, when the male lock component 118A of the cannula 110A is oriented to match its straight and curved sides with the opening 122, the male lock component 118A may pass through the opening 122. However, if the cannula 110A is rotated once the male lock component 118A is through the opening 122, the straight and curved sides no longer match up, and the male lock component 118A cannot pass back through the opening 122. The cannula 110A is accordingly interlocked with the handle 120.

Figure 2B:
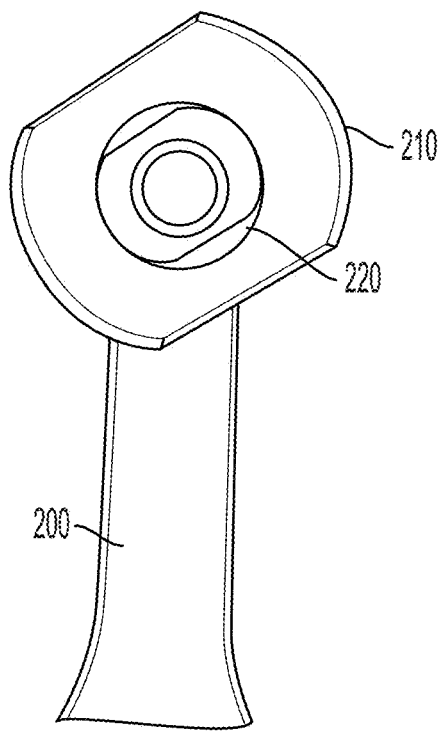

FIGS. 2A and 2B illustrate a top view of an example cannula 210 placed through an opening in the example handle 200 in an unlocked and locked position, respectively, according to an aspect of the present disclosure. In FIG. 2A, the cross-section of the male lock component of the example cannula 210 matches the opening in the handle 200. However, in FIG. 2B, the example cannula 210 is rotated and the cross-section of the male lock component no longer matches the opening in the handle 200. The male lock component of the example cannula 210, therefore, may no longer pass through the opening and the cannula 210 is interlocked with the handle 200.

FIGS. 2A and 2B additionally illustrate a top view of an example female lock component or opening 220 of the example cannula 210. In various aspects, the example female lock opening 220 is similar to the opening of the handle 200 in that it has a cross-sectional shape that matches the male lock component in one orientation, but not when the male lock component is rotated relative to the female lock opening 220. In some aspects, the female lock opening 220 includes a notch in the inner wall of the female lock opening 220 that is configured to accept the male lock component.

Figure 3A:
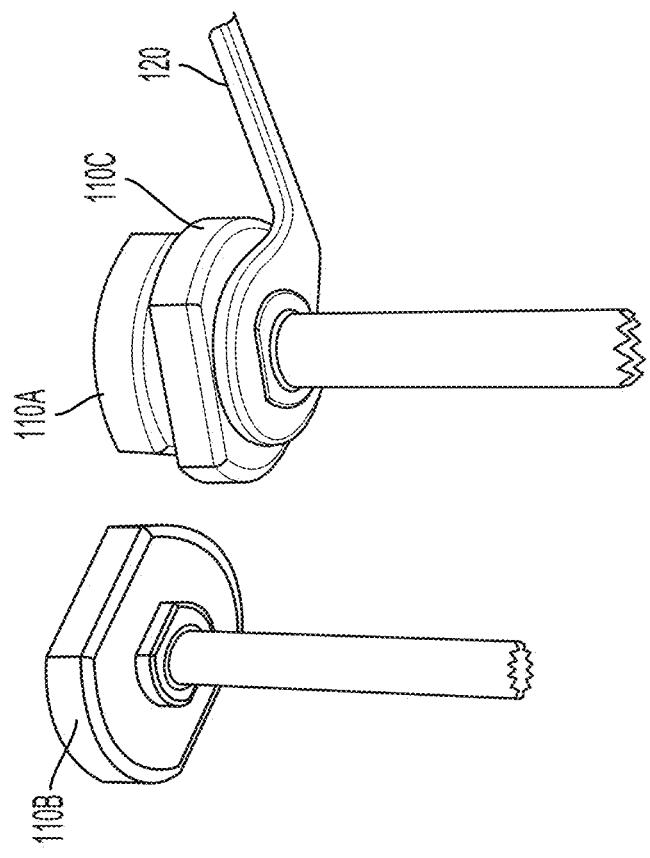
FIG. 3A illustrates a perspective view of an example configuration of nested cannulas, according to an aspect of the present disclosure.
Figure 3B:
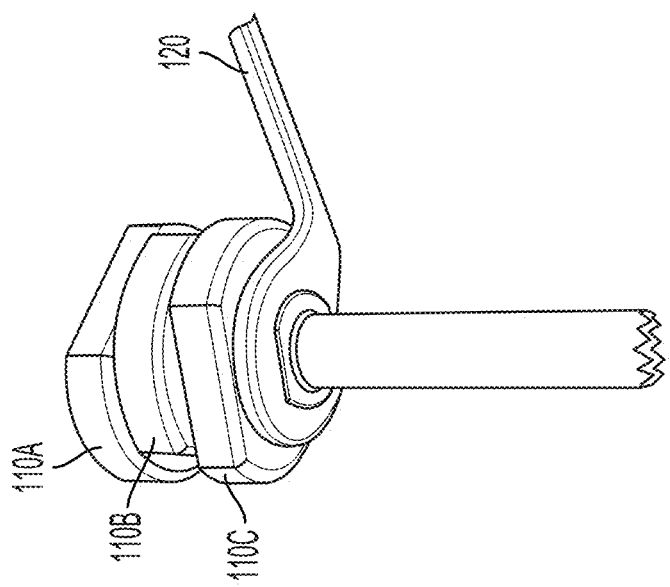
FIG. 3B illustrates a perspective view an example configuration of the nested cannulas of FIG. 3A, according to an aspect of the present disclosure.

Each cannula 110A, 110B, 110C in the cannula system 100 can be interlocked with any other cannula 110A, 110B, 110C in the cannula system 100. For example, FIGS. 3A and 3B illustrate two example orientations of the cannulas 110A, 110B, and 110C. In the example orientation of FIG. 3A, the cannula 110C is interlocked with the handle 120. The cannula 110B is nested within, and interlocked with, the cannula 110C. And, the cannula 110A is nested within, and interlocked with, the cannula 110B. In comparison, the example orientation of FIG. 3B includes the cannula 110C interlocked with the handle 120; however, the cannula 110A is nested within, and interlocked with, the cannula 110C, while the cannula 110B remains unused and off to the side. In other examples, the cannula 110B or the cannula 110A may be interlocked with the handle 120 and the cannula 110C may be unused.

The ability to interlock any of the cannulas 110A, 110B, 110C with each other or with the handle 120 provides a surgeon with greater flexibility in choosing which cannulas to use for a surgical procedure than conventional cannula systems. This increased flexibility may enable a surgeon to make smaller incisions in a patient since the surgeon is not required to use the largest cannula in a set. The increased flexibility may also lessen the weight of, and thus the force applied on the patient by, the nested cannulas since the surgeon may skip cannula sizes when nesting one cannula within another.

In some aspects of the present disclosure, the respective locking mechanisms of each cannula 110A, 110B, 110C may be identical or substantially identical. Stated differently, in such aspects, each male lock component 118A, 118B, 118C of each respective cannula 110A, 110B, 110C in the cannula system 100 are substantially identical, and each female lock opening 220 of each respective cannula 110A, 110B, 110C in the cannula system 100 are substantially identical. In an example, each male lock component 118A, 118B, 118C and each female lock opening 220 are sized equally regardless of the size of their respective cannula 110A, 110B, 110C. In such aspects, the cannulas 110A, 110B, and 110C can be considered to have a universal locking mechanism since the locking mechanism of each is the same.

In other aspects, the cannulas 110A, 110B, and 110C could have identical or substantially identical male lock components 118A, 118B, and 118C, but different female lock openings 220. In other aspects still, the cannulas 110A, 110B, and 110C could have different male lock components 118A, 118B, and 118C, but identical or substantially identical female lock openings 220. In some aspects, the smallest cannula (e.g., the cannula 110A) in the system 100 does not have a female lock opening 220 since no other cannula (e.g., the cannulas 110B and 110C) can nest within the smallest cannula.

Figure 4B:
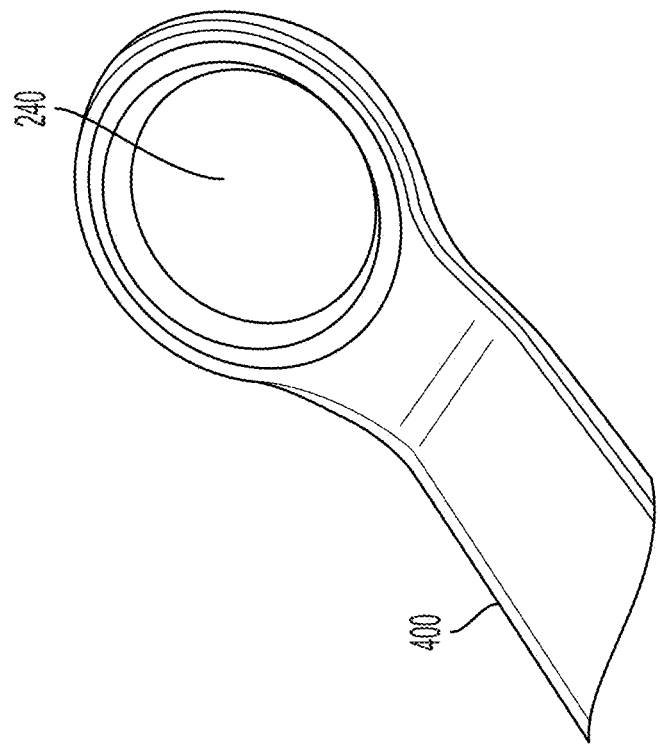
FIG. 4B illustrates a perspective view of a handle corresponding to the alternative locking mechanism of FIG. 4A, according to an aspect of the present disclosure.
Figure 4A:
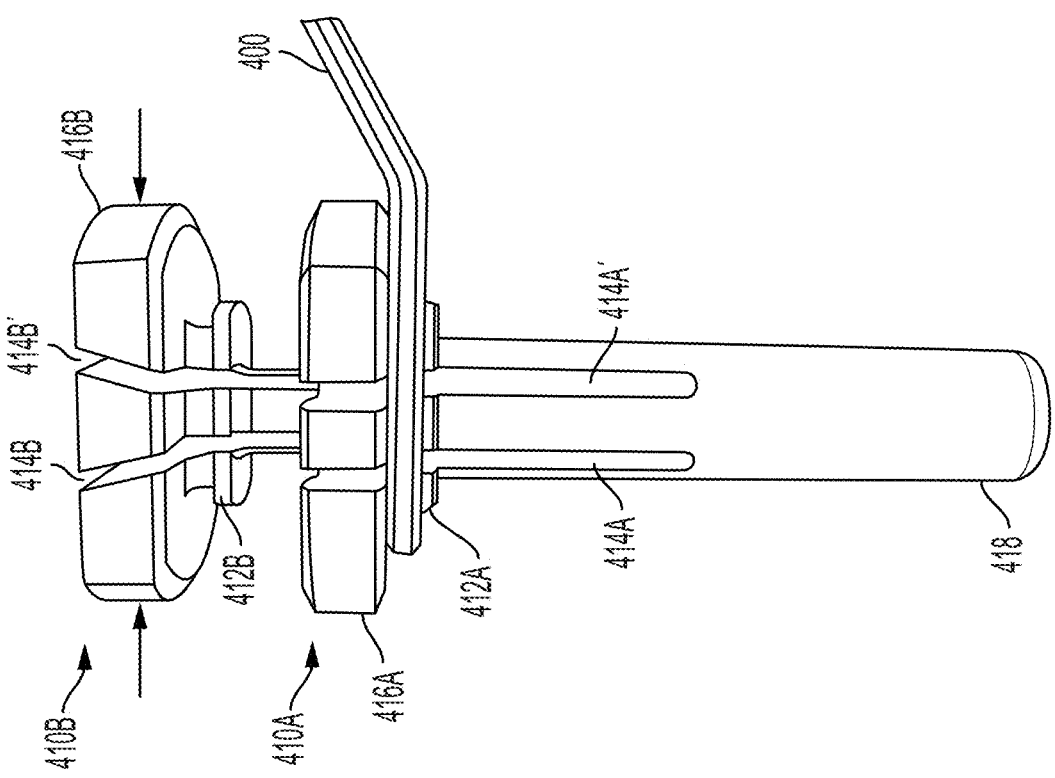
FIG. 4A illustrates a perspective view of an alternative locking mechanism, according to an aspect of the present disclosure.

In some aspects of the present disclosure, a respective locking mechanism of each cannula of the cannula system 100 may be a squeeze lock mechanism. FIG. 4A shows example cannulas 410A and 410B configured with an example squeeze lock mechanism. For instance, the example cannula 410A includes gaps 414A and 414A' that extend through the head 416A of the example cannula 410A into a portion of the tube 418 of the example cannula 410A. The gaps 414A and 414A' enable the cannula 410A to be compressed inward by applying a force on either side of the cannula 410 to reduce the size of the gaps 414A and 414A'. For example, a force may be applied to the head 416A of the cannula 410A in the direction of the arrows illustrated on the example cannula 410B. The example cannula 410A may also include an extension 412A.

Accordingly, the combination of the ability to be flexed inward and the extension 412A enable the example cannula 410A to be interlocked with the handle 400. For instance, when the cannula 410A is compressed inward, the extension 412A may be able to pass through the opening 420 (FIG. 4B) of the handle 410. However, when the compressive force is released after the extension 412A passes through the opening 420, the extension 412A extends past the outer bounds of the opening 420 and may not pass back through the opening 420. Thus, this enables the handle 400 to be interlocked with the cannula 410.

Due to the gaps 412A and 412A', the extension 412A includes multiple extension components that are broken up by the gaps 412A and 412A'. In some examples, the extension 412A may extend fully around the perimeter of the cannula 410A, except for the gaps 412A and 412A'. In some examples, the extension 412A may have a circular cross-section corresponding to the circular opening 420 of the handle 400 as illustrated in FIG. 4B. In such examples, the cannula 410A may rotate freely about its axis in either direction since the opening 420 is circular. In other examples, the extension 412A may have other cross-sectional shapes that correspond to the cross-sectional shape of the opening 420 of the handle 400, for instance, a square. In such an instance, the cannula 410A may include an extension 412A only on one or more sides of the square, such as on two sides. In such an instance, the cannula 410A is prevented from rotating about its axis since the opening 420 is square.

Similar to how the example cannula 410A may be interlocked with the handle 400, two cannulas (e.g., the cannulas 410A and 410B) may be interlocked with one another by way of the squeeze lock mechanism. In such instances, the extension 412A may be considered a male lock component and the head 416A of the cannula 410A may have a female lock component, such as an opening and a notch. For example, the example cannula 410B similarly includes gaps 414B and 414B' and an extension 412B consistent with the description above for the cannula 410A. Accordingly, the cannula 410B may be compressed inward by a force in the direction of the illustrated arrows on the head 416B of the cannula 410B. The compressive force decreases the gaps 414B and 414B' and thus allows the extension 412B to pass through the opening of the female lock component in the head 416A of the cannula 410A. Once the extension 412B passes through the opening, the compressive force may be released, increasing the gaps 414B and 414B' and allowing the extension 412B to enter a notch within the inner wall of the head 416A of the cannula 410A. When the extension 412B is within the notch, it may not pass back through the opening, and thus the cannula 410B is interlocked with the cannula 410A.

In some examples, the notch of the female lock component in the head 416A of the cannula 410A may extend around the entire perimeter of the inner wall of the head 416A. Such examples may enable the cannula 410B to rotate freely about its axis when it is nested within, and interlocked with, the cannula 410A. For instance, in some examples, the cross-section of the notch and of the extension 412B may be correspondingly circular. In some examples, the notch may extend less than the entire perimeter of the inner wall. Such examples may prevent or limit the cannula 410B from rotating about its axis when it is nested within, and interlocked with, the cannula 410A. For instance, the cannula 410A may include multiple notches that correspondingly match the multiple extension components of the extension 412B on the cannula 410B. Thus, when the extension components are placed within their respective notches, the extension components are locked within the notch and the cannula 410B is prevented from rotating. In some examples, each notch of the multiple notches may be sized larger than each extension component, although the notches are separate and do not join together. Thus, in such examples, each extension component has space to move within its respective notch and the cannula 410B may partially rotate about its axis in either direction, though it may not freely rotate a complete revolution.

In other examples, the opening and notch of the example cannula 410A may have other cross-sectional shapes that correspond to the cross-sectional shape of the extension 412B of the cannula 410B, for instance, a square. In such an instance, the cannula 410B may include an extension 412B only on one or more sides of the square, such as on two sides. In such an instance, the cannula 410B is prevented from rotating about its axis when it is nested within, and interlocked with, the cannula 410A because of the square cross-sectional shape.

Each cannula 410A, 410B may be interlocked with any other cannula 410A, 410B in an example cannula system 100 including respective squeeze lock mechanisms. In some aspects, each respective squeeze lock mechanism on each cannula 410A, 410B may be sized equally.

In some aspects of the present disclosure, the respective locking mechanisms of the each cannula 110A, 110B, 110C may be configured so as to enable an ordered release or disengagement of the nested and interlocked cannulas 110A, 110B, 110C from one another. The advantages of such aspects may be exemplified by the following situation. A surgeon may insert the cannulas 110A, 110B, and 110C in the orientation of FIG. 3A at least partially into a patient. The surgeon may later desire to only disengage and remove the cannula 110A from the cannula 110B, while the cannula 110B remains nested within and interlocked with the cannula 110C and the cannula 110C remains interlocked with the handle 120. In some aspects, a surgeon may need to immobilize the cannula 110B (e.g., hold it with one hand) while disengaging or removing (e.g., with the surgeon's other hand) the cannula 110A so that the cannula 110B does not also disengage from the cannula 110C and the cannula 110C does not disengage from the handle 120.

It would be advantageous, however, if the surgeon were able to disengage the cannula 110A using only one hand to free the surgeon's other hand during surgery. Accordingly, aspects with cannulas 110A, 110B, 110C that enable an ordered release include respective locking mechanisms that require different amounts of force to disengage the various combinations of nesting orientations of the cannulas 110A, 110B, and 110C and the handle 120. For example, in the orientation of FIG. 3A, it may require less force to disengage the cannula 110A from the cannula 110B than it does to disengage the cannula 110B from the cannula 110C. And it requires less force to disengage cannulas 110A, 110B, or 110C from one another than it does to disengage a cannula 110B, 110B, or 110C from the handle 120. In this way, the surgeon can disengage and remove the cannula 110A from the cannula 110B without having to immobilize the cannula 110B, and without disengaging the cannula 110B from the cannula 110C or the cannula 110C from the handle 120, by applying a force (e.g., twist or pull) to the cannula 110A that is sufficient to disengage the cannula 110A from the cannula 110B but insufficient to disengage the cannula 110B from the cannula 110C or the cannula 110C from the handle 120. The surgeon may apply such force using only one hand.

Figure 6:
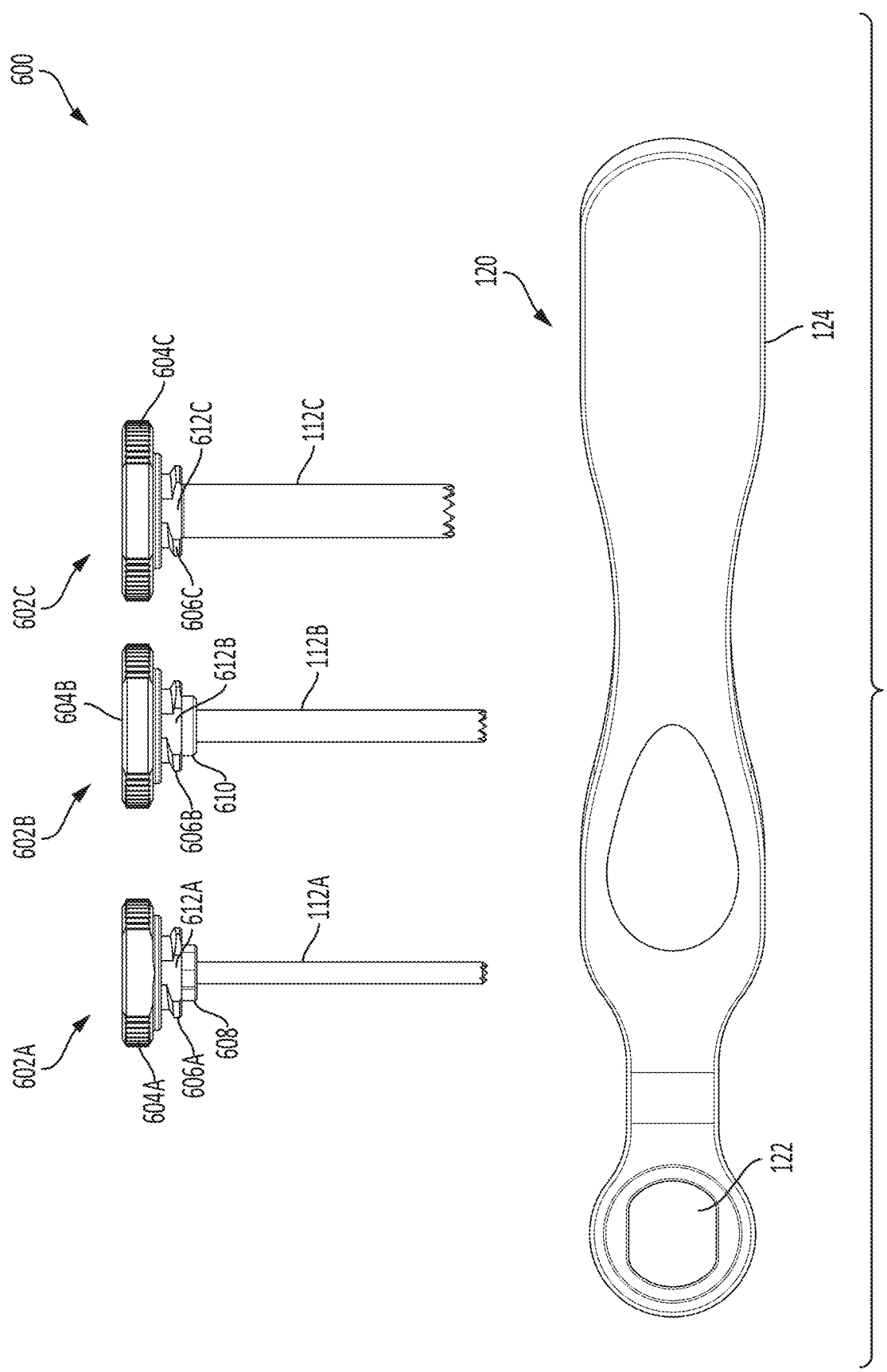
FIG. 6 illustrates a perspective view of a cannula system including cannulas having respective twist locking mechanisms constructed for ordered release, according to an aspect of the present disclosure.

FIGS. 6 to 9 illustrate views of an example cannula system 600 including cannulas 602A, 602B, and 602C having respective twist lock mechanisms constructed for ordered release. Referring to FIG. 6, in various aspects, the example cannula system 600 includes a cannula 602A, a cannula 602B, and a cannula 602C, though in other aspects the cannula system 600 may include additional cannulas, as described similarly for the cannula system 100 discussed above. In at least some aspects, the system 600 includes a handle 120. The handle 120 is described above. The cannulas 602A, 602B, and 602C are sized in a sequence of smaller cannulas to larger cannulas. For instance, the cannula 602C includes a tube 112C which has a larger diameter than the tube 112B of the cannula 602B, which has a larger diameter than the tube 112A of the cannula 602A. In aspects in which the cannula system 600 includes more than three cannulas 602A, 602B, 602C, the sequence may further include a cannula larger than the cannula 602C or a cannula smaller than the cannula 602A, and so forth.

Figure 7:
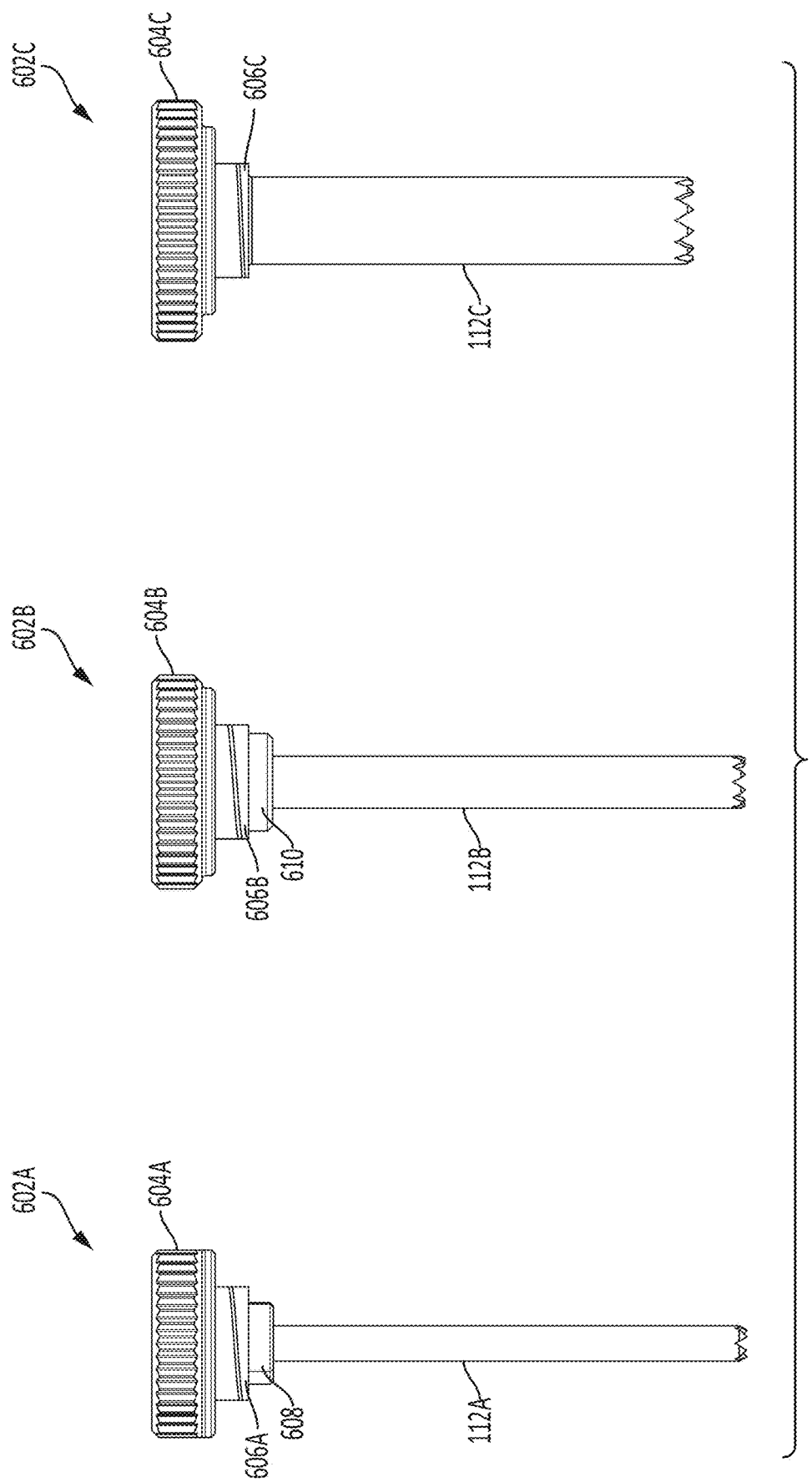
FIG. 7 illustrates a side view of the cannulas of FIG. 6, according to an aspect of the present disclosure.
Figure 8:
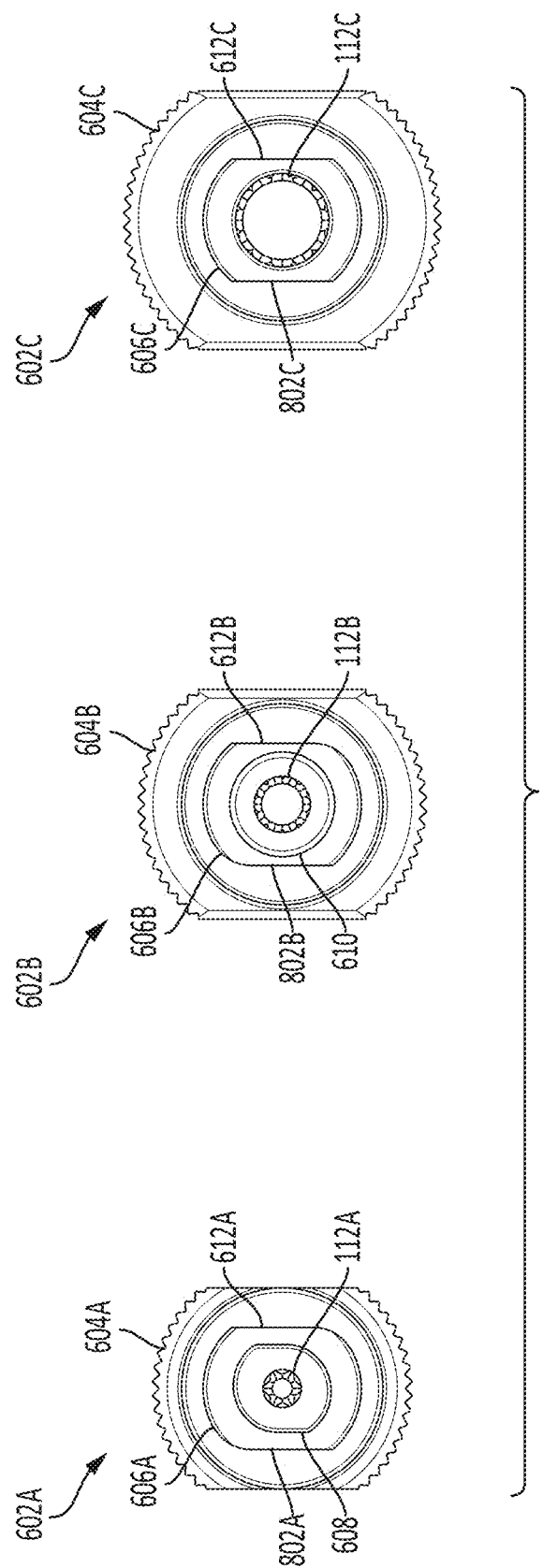
FIG. 8 illustrates a bottom view of the cannulas of FIG. 6, according to an aspect of the present disclosure.
Figure 9:
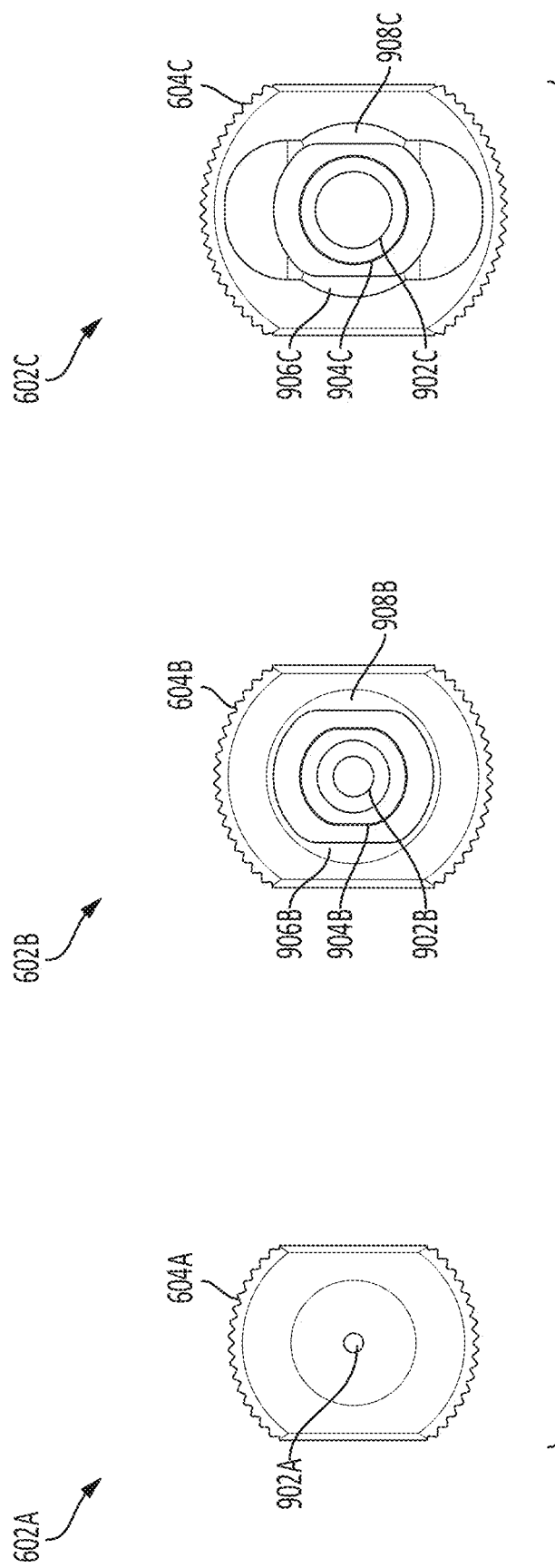
FIG. 9 illustrates a top view of the cannulas of FIG. 6, according to an aspect of the present disclosure.

In at least some aspects, the cannula 602A includes a male lock component having a thread 606A and a cam 608. The male lock component of the cannula 602A may be integral with or attached to a head 604A of the cannula 602A. In some examples, the head 604A may include teeth or another suitable grip-enhancing construction or material. In at least some aspects, the thread 606A is split into two portions. For example, the thread 606A may be split by opposing flat surfaces 612A and 802A (FIG. 8). FIG. 7 illustrates the cannula 602A rotated ninety degrees relative to the illustrated cannula 602A in FIG. 6 to show the thread pitch of the thread 606A. FIG. 8 illustrates a bottom view of the cannula 602A. In at least some aspects, the cam 608 may have the shape illustrated in FIG. 8, though in other aspects may have other suitable shapes. FIG. 9 illustrates a top view of the cannula 602A showing an opening to a channel 902A that extends through the tube 112A of the cannula 602A. In this example, the cannula 602A is the smallest cannula in the system 600 and does not include a female lock component or opening.

Returning to FIG. 6, in various aspects, the cannula 602B includes a male lock component having a thread 606B. In at least some examples, the male lock component of the cannula 602B does not include a cam. In some aspects, the male lock component of the cannula 602B instead includes a support member 610. In such aspects, the support member 610 can help in maintaining concentricity of the cannula 602B with the cannula 602C when nested within the cannula 602C. FIG. 8 illustrates a bottom view of the cannula 602B. In some aspects, such as the illustrated aspect, the support member 610 may have a circular shape.

Returning to FIG. 6, the male lock component of the cannula 602B may be integral with or attached to a head 604B of the cannula 602B. In some examples, the head 604B may include teeth or another suitable grip-enhancing construction or material. In at least some aspects, the thread 606B is split into two portions. For example, the thread 606B may be split by opposing flat surfaces 612B and 802B (FIG. 8). FIG. 7 illustrates the cannula 602B rotated ninety degrees relative to the illustrated cannula 602B in FIG. 6 to show the thread pitch of the thread 606B. In at least some aspects, the thread pitch of the thread 606B is equal to the thread pitch of the thread 606A of the cannula 602A. FIG. 9 illustrates a top view of the cannula 602B showing an opening to a channel 902B that extends through the tube 112B of the cannula 602B. The cannula 602B includes a female lock component/opening having a notch 904B. The notch 904B has a shape that suitably corresponds to the cam 608 of the cannula 602A. In some aspects, the female lock component/opening of the cannula 602B includes a female thread (not shown) that extends into the sidewalls 906B and 908B of the head 604B.

Returning to FIG. 6, in various aspects, the cannula 602C includes a male lock component having a thread 606C. The male lock component of the cannula 602C may be integral with or attached to a head 604C of the cannula 602C. In some examples, the head 604C may include teeth or another suitable grip-enhancing construction or material. In at least some aspects, the thread 606C is split into two portions. For example, the thread 606C may be split by opposing flat surfaces 612C and 802C (FIG. 8). FIG. 7 illustrates the cannula 602C rotated ninety degrees relative to the illustrated cannula 602C in FIG. 6 to show the thread pitch of the thread 606C. In at least some aspects, the thread 606C has a smaller thread pitch than the thread 606A of the cannula 602A and the thread 606B of the cannula 602B. FIG. 8 illustrates a bottom view of the cannula 602C.

FIG. 9 illustrates a top view of the cannula 602C showing an opening to a channel 902C that extends through the tube 112C of the cannula 602C. The cannula 602C includes a female lock component/opening. In at least some aspects, the female lock component/opening of the cannula 602C includes a notch 904B. In such aspects, the notch 904B is sized and shaped such that it does not suitably correspond to the size and shape of the cam 608 of the cannula 602A. The notch 904B may, in some instances, be sized and shaped to correspond to the support member 610 of the cannula 602B, which may help the main concentricity of the cannula 602B and the cannula 602C when the cannula 602B is nested within the cannula 602C. In at least some aspects, the female lock component/opening of the cannula 602C includes a female thread (not shown) that extends into the sidewalls 906C and 908C of the head 604C.

The interaction of the cannulas 602A, 602B, and 602C will now be described. The cam 608 of the male lock component of the cannula 602A can engage with the sidewall of the notch 904B of the female lock component/opening of the cannula 602B, for instance by rotating the cannula 602A when nested within the cannula 602B. The engagement of the cam 608 with the sidewall of the notch 904B interlocks the cannula 602A with the cannula 602B. The cam 608, however, will not engage with the sidewall of the notch 904C of the female lock component/opening of the cannula 602C.

The thread 606A of the male lock component of the cannula 602A does not engage the female thread extending into the sidewalls 906B and 908B of the female lock component/opening of the cannula 602B. Rather, the thread 606A merely fits within the female thread of the cannula 602B. For example, if the cannula 602A is rotated just past the cam 608 becoming disengaged from the sidewall of the notch 904B, the female thread of the cannula 602B will prevent a surgeon from translating the cannula 602A along the long axis of the cannulas 602A and 602B to remove the cannula 602A from the cannula 602B; however, the cannula 602A will be loose to translate back and forth along that long axis because the thread 606A is not engaged with the female thread of the cannula 602B. Once the cannula 602A is rotated further, the thread 606A becomes clear of the female thread of the cannula 602B and the surgeon may remove the cannula 602A from the cannula 602B. In this way, while the female thread of the cannula 602B does not contribute to the engagement of the cannula 602A with the cannula 602B, and therefore does not contribute to the torque required to disengage the cannula 602A from the cannula 602B, the female thread of the cannula 602B can help maintain the connection between the cannula 602A and the cannula 602B during surgery if the cam 608 were to accidentally become disengaged from the sidewall of the notch 904B.

Conversely, the thread 606A of the cannula 602A does engage the female thread of the female lock component/opening of the cannula 602C. The engagement of the thread 606A with the female thread interlocks the cannula 602A with the cannula 602C. As stated above, the cam 608 of the cannula 602A does not engage with the female lock component/opening of the cannula 602C. The thread 606A of the cannula 602A is also able to interlock with the handle 120 at the opening 122.

In addition, the thread 606B of the male lock component of the cannula 602B engages the female thread of the female lock component/opening of the cannula 602C. The engagement of the thread 606B with the female thread interlocks the cannula 602B with the cannula 602C. The thread 606B is also able to interlock with the handle 120 at the opening 122. The thread 606C of the male lock component of the cannula 602C is additionally able to interlock with the handle 120 at the opening 122.

The above-described respective male lock components and female lock components/openings of the cannulas 602A, 602B, and 602C enable for an ordered release or disengagement of the cannulas 602A, 602B, and 602C. In an example, the cannula 602A is nested within, and interlocked with the cannula 602B, which is nested within, and interlocked with the cannula 602C, which is interlocked with the handle 120. In this example, it requires less rotational force to disengage the cam 608 of the cannula 602A from the notch 904B of the female lock component/opening of the cannula 602B than it does to disengage the thread 606B of the cannula 602B from the female thread of the female lock component/opening of the cannula 602C. It also requires less rotational force to disengage the cam 608 from the notch 904B than it does to disengage the thread 606C of the cannula 602C from the handle 120. In this way, a surgeon can disengage and remove the cannula 602A from the cannula 602B using one hand without disengaging the cannula 602B or the cannula 602C.

Continuing with this example with the cannula 602A removed, it requires less rotational force to disengage the thread 606B of the cannula 602B from the female thread of the female lock component/opening of the cannula 602C than it does to disengage the thread 606C of the cannula 602C from the handle 120. In this way, a surgeon can disengage and remove the cannula 602B from the cannula 602C using one hand without disengaging the cannula 602C. This is true whether or not the cannula 602A is interlocked with cannula 602B.

In some instances, the cannula 602A may be nested within, and interlocked with, the cannula 602C, which is interlocked with the handle 120. In such instances, it requires less rotational force to disengage the thread 606A of the cannula 602A from the female thread of the female lock component/opening of the cannula 602C than it does to disengage the thread 606C of the cannula 602C from the handle 120. In this way, a surgeon can disengage and remove the cannula 602A from the cannula 602C using one hand without disengaging the cannula 602C. In some instances, the cannula 602A may be nested within, and interlocked with, the cannula 602B, which is interlocked with the handle 120. In such instances, it requires less rotational force to disengage the cam 608 of the cannula 602A from the notch 904B of the female lock component/opening of the cannula 602B than it does to disengage the thread 606B of the cannula 602B from the handle 120. In this way, a surgeon can disengage and remove the cannula 602A from the cannula 602B using one hand without disengaging the cannula 602B.

Figure 10:
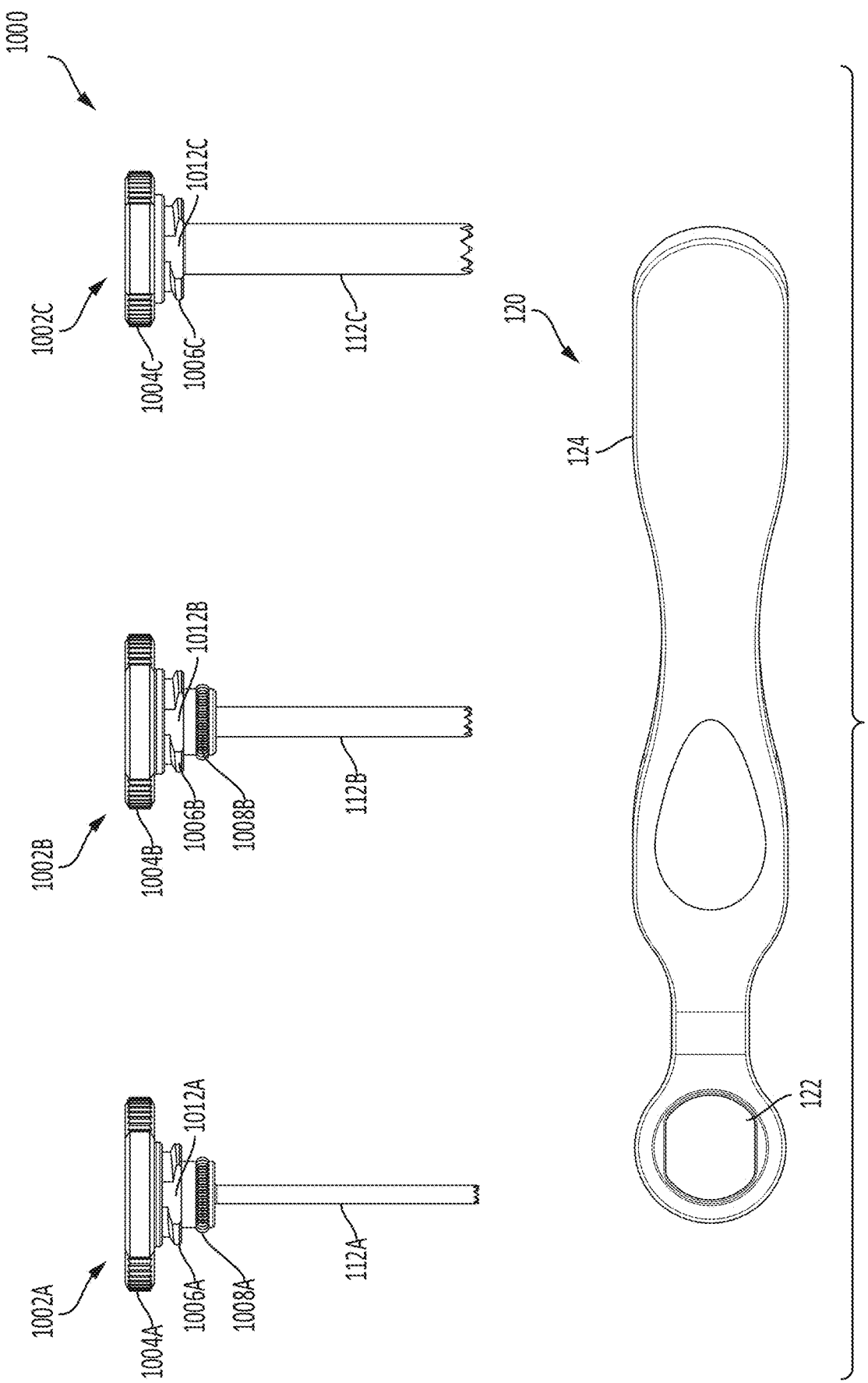
FIG. 10 illustrates a perspective view of a cannula system including cannulas having respective spring-and-thread locking mechanisms constructed for ordered release, according to an aspect of the present disclosure.

FIGS. 10 to 13 illustrate views of an example cannula system 1000 including cannulas 1002A, 1002B, and 1002C having respective spring-and-thread lock mechanisms constructed for ordered release. Referring to FIG. 10, in various aspects, the example cannula system 1000 includes a cannula 1002A, a cannula 1002B, and a cannula 1002C, though in other aspects the cannula system 1000 may include additional cannulas, as described similarly for the cannula systems 100 and 600 discussed above. In at least some aspects, the system 1000 includes a handle 120. The handle 120 is described above. The cannulas 1002A, 1002B, and 1002C are sized in a sequence of smaller cannulas to larger cannulas. For instance, the cannula 1002C includes a tube 112C, which has a larger diameter than the tube 112B of the cannula 1002B, which has a larger diameter than the tube 112A of the cannula 1002A. In aspects in which the cannula system 1000 includes more than three cannulas 1002A, 1002B, 1002C, the sequence may further include a cannula larger than the cannula 1002C or a cannula smaller than the cannula 1002A, and so forth.

In at least some aspects, the cannula 1002A includes a male lock component having a thread 1006A and a spring 1008A. At least a portion of the male lock component of the cannula 1002A may be integral with or attached to a head 1004A of the cannula 1002A. In some examples, the head 1004A may include teeth or another suitable grip-enhancing construction or material. In at least some aspects, the spring 1008A is a canted coil spring. In various examples, the spring 1008A is partially positioned within a notch of the male lock component of the cannula 1002A such that the spring 1008A extends beyond a directly adjacent surface of the male lock component and is prevented from axial movement along the cannula 1002A. In some aspects, the spring 1008A is attached to the male lock component of the cannula 1002A. In other aspects, the spring 1008A is merely maintained within the notch of the male lock component of the cannula 1002A and is not otherwise attached to the male lock component.

Figure 11:
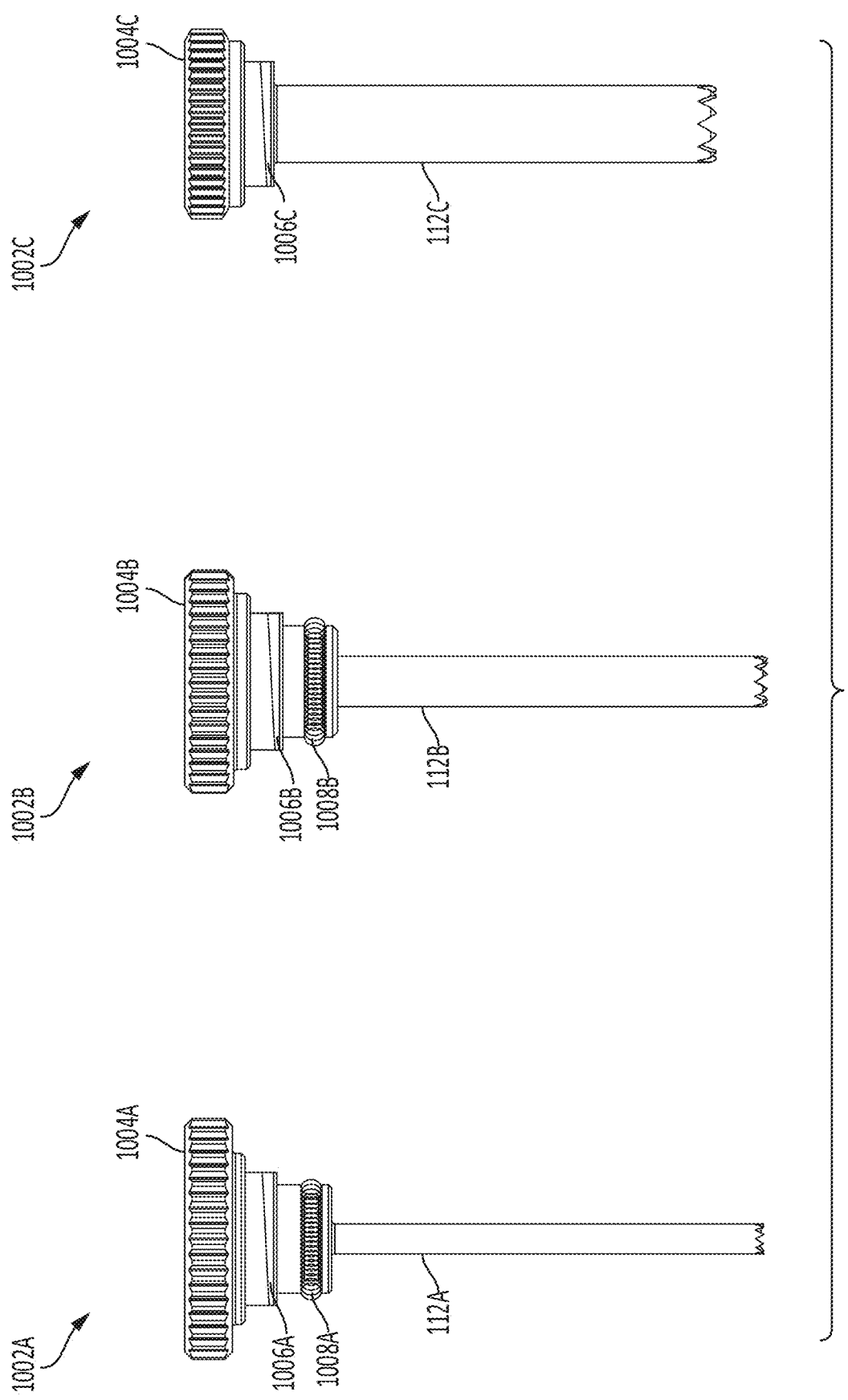
FIG. 11 illustrates a side view of the cannulas of FIG. 10, according to an aspect of the present disclosure.
Figure 12:
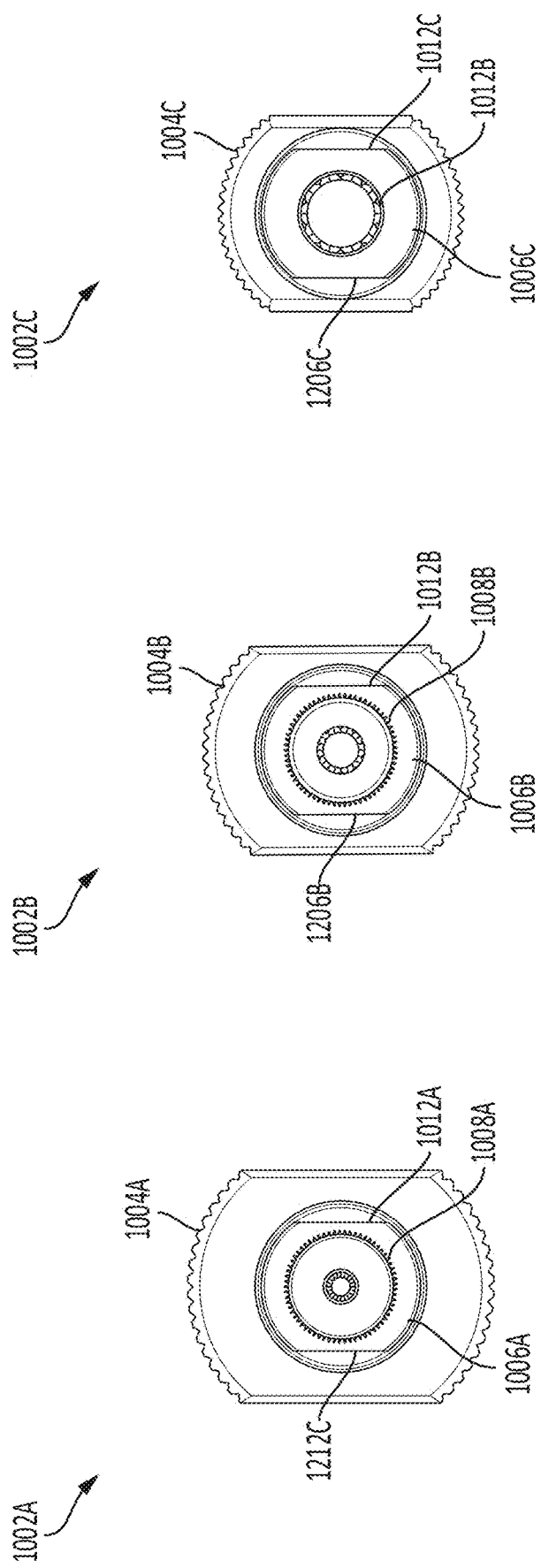
FIG. 12 illustrates a bottom view of the cannulas of FIG. 10, according to an aspect of the present disclosure.

In at least some aspects, the thread 1006A of the male lock component of the cannula 1002A is split into two portions. For example, the thread 1006A may be split by opposing flat surfaces 1012A and 1202A (FIG. 12). FIG. 11 illustrates the cannula 1002A rotated ninety degrees relative to the illustrated cannula 1002A in FIG. 10 to show the thread pitch of the thread 1006A. FIG. 12 illustrates a bottom view of the cannula 1002A that shows the opposing flat surfaces 1012A and 1202A. The bottom view also illustrates that only a portion of the spring 1008A is visible due to the spring 1008A being positioned partially within the notch of the male lock component of the cannula 1002A. FIG. 13 illustrates a top view of the cannula 1002A showing an opening to a channel 1002A that extends through the tube 112A of the cannula 1002A. In this example, the cannula 1002A is the smallest cannula in the system 1000 and does not include a female lock component or opening.

Returning to FIG. 10, in at least some aspects, the cannula 1002B includes a male lock component having a thread 1006B and a spring 1008B. At least a portion of the male lock component of the cannula 1002B may be integral with or attached to a head 1004B of the cannula 1002B. In some examples, the head 1004B may include teeth or another suitable grip-enhancing construction or material. In at least some aspects, the spring 1008B is a canted coil spring. In various examples, the spring 1008B is partially positioned within a notch of the male lock component of the cannula 1002B such that the spring 1008B extends beyond a directly adjacent surface of the male lock component and is prevented from axial movement along the cannula 1002B. In some aspects, the spring 1008B is attached to the male lock component of the cannula 1002B. In other aspects, the spring 1008B is merely maintained within the notch of the male lock component of the cannula 1002B and is not otherwise attached to the male lock component.

In at least some aspects, the thread 1006B of the male lock component of the cannula 1002B is split into two portions. For example, the thread 1006B may be split by opposing flat surfaces 1012B and 1202B (FIG. 12). FIG. 11 illustrates the cannula 1002B rotated ninety degrees relative to the illustrated cannula 1002B in FIG. 10 to show the thread pitch of the thread 1006B. FIG. 12 illustrates a bottom view of the cannula 1002B that shows the opposing flat surfaces 1012B and 1202B. The bottom view also illustrates that only a portion of the spring 1008B is visible due to the spring 1008B being positioned partially within the notch of the male lock component of the cannula 1002B. FIG. 13 illustrates a top view of the cannula 1002B showing an opening to a channel 1002B that extends through the tube 112B of the cannula 1002B. The top view also shows a female lock component/opening of the cannula 1002B. In at least some aspects, the female lock component/opening of the cannula 1002B includes a notch 1304B. The notch 1304B is sized and shaped in relation to the spring 1008A of the cannula 1002A. In at least some aspects, the female lock component/opening of the cannula 1002B includes a notch 1306B. The notch 1306B is sized and shaped to enable space for the thread 1006A of the cannula 1002A, though the notch 1306B does not engage the thread 1006A.

Returning to FIG. 10, in at least some aspects, the cannula 1002C includes a male lock component having a thread 1006C. In this example, the cannula 1002C is the largest cannula in the set of cannulas of the system 1000 and therefore its male lock component does not need to include a spring since the cannula 1002C cannot nest within any other cannula in the set, though the male lock component of the cannula 1002C could include a spring. At least a portion of the male lock component of the cannula 1002C may be integral with or attached to a head 1004C of the cannula 1002C. In some examples, the head 1004C may include teeth or another suitable grip-enhancing construction or material. In at least some aspects, In at least some aspects, the thread 1006C of the male lock component of the cannula 1002C is split into two portions. For example, the thread 1006C may be split by opposing flat surfaces 1012C and 1202C (FIG. 12). FIG. 11 illustrates the cannula 1002C rotated ninety degrees relative to the illustrated cannula 1002C in FIG. 10 to show the thread pitch of the thread 1006C. In various aspects, the thread 1006A of the cannula 1002A, the thread 1006B of the cannula 1002B, and the thread 1006C of the cannula 1002C have equal thread pitches. FIG. 12 illustrates a bottom view of the cannula 1002C that shows the opposing flat surfaces 1012C and 1202C.

FIG. 13 illustrates a top view of the cannula 1002C showing an opening to a channel 1002C that extends through the tube 112C of the cannula 1002C. The top view also shows a female lock component/opening of the cannula 1002C. In at least some aspects, the female lock component/opening of the cannula 1002C includes a notch 1304C. The notch 1304C is sized and shaped in relation to the spring 1008A of the cannula 1002A and the spring 1008B of the cannula 1002B. Stated differently, the spring 1008A and the spring 1008B may be sized and shaped the same so that the notch 1304C is sized and shaped in relation to each the spring 1008A and the spring 1008B. In at least some aspects, the female lock component/opening of the cannula 1002C includes a notch 1306C. The notch 1306C is sized and shaped to enable space for the thread 1006A of the cannula 1002A or the thread 1006B of the cannula 1002B, though the notch 1306C does not engage the thread 1006A nor the thread 1006B.

The interaction of the cannulas 1002A, 1002B, and 1002C will now be described. The spring 1008A of the male lock component of the cannula 1002A can engage with the sidewall of the notch 1304B of the female lock component/opening of the cannula 1002B, for instance by translating (e.g., pushing) the cannula 1002A along an axial direction when nested within the cannula 1002B. The spring 1008A is sized larger than the notch 1304B, and as the spring 1008A is forced into the notch 1304B, the spring 1008A is compressed. The counteracting force of the compressed spring 1008A against the sidewall of the notch 1304B interlocks the cannula 1002A with the cannula 1002B. To disengage the compressed spring 1008A from the sidewall of the notch 1304B, the cannula 1002A may be translated (e.g., pulled) along the opposite axial direction as when the spring 1008A was engaged with the sidewall. The spring 1008A of the male lock component of the cannula 1002A can engage with the sidewall of the notch 1304C of the female lock component/opening of the cannula 1002C in a similar manner, which interlocks the cannula 1002A with the cannula 1002C. The thread 1006A of the male component of the cannula 1002A is able to interlock (e.g., via rotational engagement) with the handle 120 at the opening 122.

In addition, the spring 1008B of the male lock component of the cannula 1002B can engage with the sidewall of the notch 1304B of the female lock component/opening of the cannula 1002C, for instance by translating (e.g., pushing) the cannula 1002B along an axial direction when nested within the cannula 1002C. The spring 1008B is sized larger than the notch 1304C, and as the spring 1008B is forced into the notch 1304C, the spring 1008B is compressed. The counteracting force of the compressed spring 1008B against the sidewall of the notch 1304C interlocks the cannula 1002B with the cannula 1002C. To disengage the compressed spring 1008B from the sidewall of the notch 1304C, the cannula 1002B may be translated (e.g., pulled) along the opposite axial direction as when the spring 1008B was engaged with the sidewall. The thread 1006B of the male component of the cannula 1002B is able to interlock (e.g., via rotational engagement) with the handle 120 at the opening 122. The thread 1006C of the male component of the cannula 1002C is also able to interlock (e.g., via rotational engagement) with the handle 120 at the opening 122.

The above-described respective male lock components and female lock components/openings of the cannulas 1002A, 1002B, and 1002C enable for an ordered release or disengagement of the cannulas 1002A, 1002B, and 1002C. In an example, the cannula 1002A is nested within, and interlocked with the cannula 1002B, which is nested within, and interlocked with the cannula 1002C, which is interlocked with the handle 120. In this example, it requires less translational (e.g., pulling) force to disengage the spring 1008A of the cannula 1002A from the sidewall of the notch 1304B of the female lock component/opening of the cannula 1002B than it does to disengage the spring 1008B of the cannula 1002B from the sidewall of the notch 1304C of the female lock component/opening of the cannula 1002C.

Additionally, since the cannula 1002A is translated (e.g., pulled) to disengage and remove it from the cannula 1002A, such translational motion does not apply sufficient rotational force to disengage the thread 1006C of the cannula 1002C from the handle 120. In this way, a surgeon can disengage and remove the cannula 1002A from the cannula 1002B using one hand without disengaging the cannula 1002B or the cannula 1002C.

Continuing with this example with the cannula 1002A removed, the spring 1008B of the cannula 1002B can be disengaged from the sidewall of the notch 1304C of the female lock component/opening of the cannula 1002C by translating (e.g., pulling) the cannula 1002B along the axial direction. Since the cannula 1002B is translated (e.g., pulled) to disengage and remove it from the cannula 1002C, such translational motion does not apply sufficient rotational force to disengage the thread 1006C of the cannula 1002C from the handle 120. In this way, a surgeon can disengage and remove the cannula 1002B from the cannula 1002C using one hand without disengaging the cannula 1002C.

In some instances, the cannula 1002A may be nested within, and interlocked with, the cannula 1002C, which is interlocked with the handle 120. The spring 1008A of the cannula 1002A can be disengaged from the sidewall of the notch 1304C of the female lock component/opening of the cannula 1002C by translating (e.g., pulling) the cannula 1002A along the axial direction. Since the cannula 1002A is translated (e.g., pulled) to disengage and remove it from the cannula 1002C, such translational motion does not apply sufficient rotational force to disengage the thread 1006C of the cannula 1002C from the handle 120. In this way, a surgeon can disengage and remove the cannula 1002A from the cannula 1002C using one hand without disengaging the cannula 1002C.

In some instances, the cannula 1002A may be nested within, and interlocked with, the cannula 1002B, which is interlocked with the handle 120. The spring 1008A of the cannula 1002A can be disengaged from the sidewall of the notch 1304B of the female lock component/opening of the cannula 1002B by translating (e.g., pulling) the cannula 1002A along the axial direction. Since the cannula 1002A is translated (e.g., pulled) to disengage and remove it from the cannula 1002B, such translational motion does not apply sufficient rotational force to disengage the thread 1006B of the cannula 1002B from the handle 120. In this way, a surgeon can disengage and remove the cannula 1002A from the cannula 1002B using one hand without disengaging the cannula 1002B.

In some aspects of the present disclosure, each cannula in the set of cannulas of the provided system (e.g., the cannula system 100, 600, or 1000) may be constructed of a particular material to help enable an ordered release of nested and interlocked cannulas. For example, in the example cannula system 600, the cannula 602A and the cannula 602B may be constructed of a heat treated 17-4 stainless steel, the cannula 602C may be constructed of a Custom 455® heat treated stainless steel, and the handle 120 may be constructed of a commercially pure, grade 4 titanium (titanium CP4). Friction between the different materials in this example helps differentiate the rotational force required to disengage the one cannula from another. For instance, the interface between Custom 455® heat treated stainless steel and titanium CP4 has a greater static friction coefficient than the interface between heat treated 17-4 stainless steel and heat treated 17-4 stainless steel, which leads to a greater force needed to overcome the friction between Custom 455® heat treated stainless steel and titanium CP4.

Figure 5:
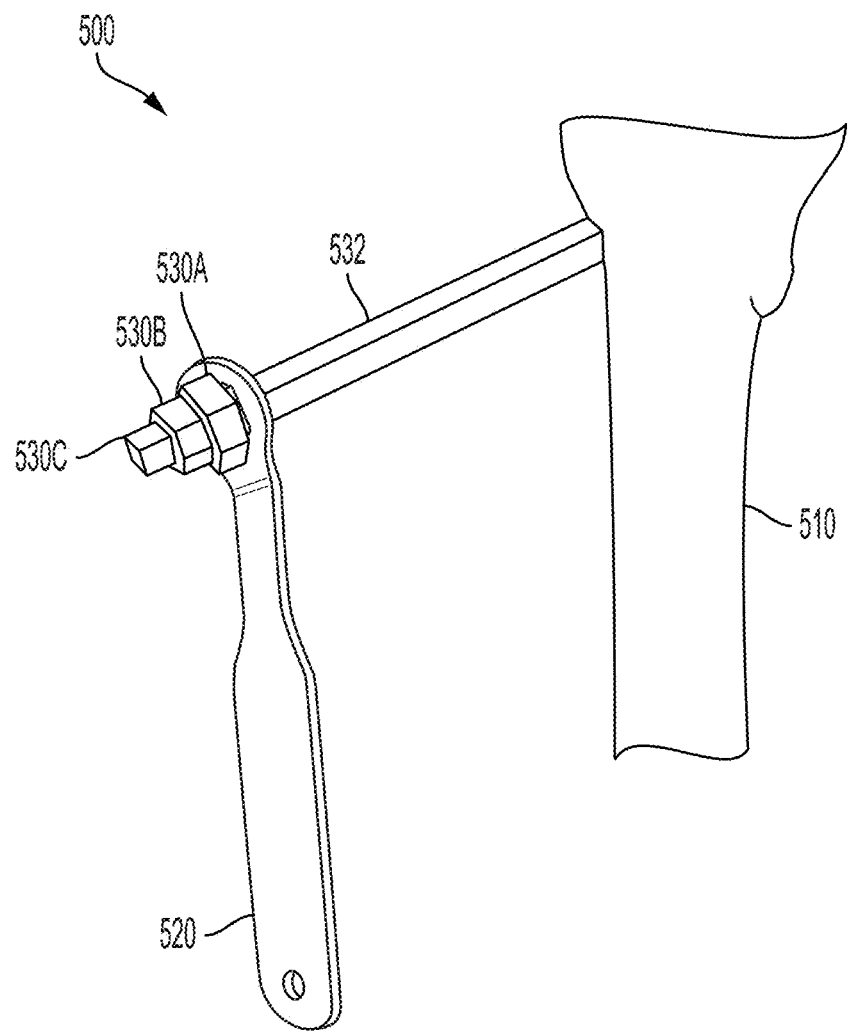
FIG. 5 illustrates an example procedure using a cannula system, according to an aspect of the present disclosure.

FIG. 5 shows an example procedure 500 that includes inserting nested cannulas into a drilled bone hole, according to an aspect of the present disclosure. Alternatively, the procedure 500 may be used external to the bone, protecting the surrounding tissues (e.g., in areas of sensitive soft tissue structures like nerves, where repeated insertion of instrumentation is most likely to cause harm and where surgical duration is important) for the sharp instruments passing through the cannulas.

In other aspects, many other methods of performing the acts described in connection with FIG. 5 may be used. For example, the order of some of the steps may be changed, certain steps may be combined with other steps, one or more of the steps may be repeated, and some of the steps described may be optional. In the example procedure 500, a surgeon may first determine the cannula sizes that the surgeon will need. In some instances, the surgeon may then nest the cannulas accordingly, if needed, for the size of the first instrument to be used. For example, the surgeon may nest the cannula 530B within the cannula 530A and the cannula 530C within the cannula 530B so that the size of the cannula 530C may be used with the first instrument.

In some instances, the surgeon may then drill a hole in the bone 510 corresponding to the largest cannula needed. For example, the cannula 530A with the tube 532 is illustrated as the largest cannula used in the example procedure 500. Thus, in this instance, the bone hole will be drilled corresponding to the size of the tube 532. In some instances, the surgeon may then interlock the handle with largest, outermost cannula to be inserted. For example, the surgeon may interlock the handle 520 with the cannula 530A. The surgeon may then insert the one or more cannulas through the bone hole. For example, the surgeon may insert the nested cannulas 530A, 530B, and 530C into the hole in the bone 510.

In some instances, the surgeon may then insert an instrument through the innermost cannula's channel and perform a portion of the example procedure 500. For example, the surgeon may insert an instrument through the channel of the cannula 530C. At subsequent points in the example procedure 500, the surgeon may remove one or more cannulas, or insert one or more cannulas, so that the surgeon may use a larger or smaller instrument that requires a larger or smaller cannula channel. For example, the surgeon may remove the cannula 530C from the cannula 530B, for instance by twisting the cannula 530C to disengage the locking mechanism with cannula 530B, so that the surgeon may access the channel in the cannula 530B with a second instrument. At a subsequent time in the example procedure 500, the surgeon may then remove the cannula 530B from the cannula 530A, for instance by twisting the cannula 530B to disengage the locking mechanism with cannula 530A, so that the surgeon may access the channel in the cannula 530A with a third instrument. At a subsequent time in the example procedure 500, the surgeon may then insert the cannula 530C into the cannula 530A and interlock them together, for instance by twisting the cannula 530C to engage the locking mechanism, so that the surgeon may again use the first instrument.

Without further elaboration, it is believed that one skilled in the art can use the preceding description to utilize the claimed inventions to their fullest extent. The examples and embodiments disclosed herein are to be construed as merely illustrative and not a limitation of the scope of the present disclosure in any way. It will be apparent to those having skill in the art that changes may be made to the details of the above-described embodiments without departing from the underlying principles discussed. In other words, various The invention is claimed as follows:

1. An interlocking cannula system comprising:
a plurality of cannulas comprising a first cannula, a second cannula, and a third cannula, wherein the first cannula is smaller than the second cannula and the third cannula, and the second cannula is smaller than the third cannula, thereby allowing the first cannula to be nested within the second cannula and/or the third cannula,
wherein each of the plurality of cannulas includes a respective locking mechanism, which allows the first cannula to be interlocked with the third cannula without the second cannula therebetween and which allows the second cannula to be interlocked with the third cannula,
wherein the respective locking mechanisms are configured such that interlocking one cannula of the plurality of cannulas with another cannula of the plurality of cannulas includes rotating the one cannula with respect to the other cannula.

2. The interlocking cannula system of claim 1, wherein the plurality of cannulas are configured to allow the first cannula to be removed from the second cannula while the second cannula remains nested within, and interlocked with, the third cannula.

3. The interlocking cannula system of claim 1, wherein the respective locking mechanisms of each of the plurality of cannulas are substantially identical.

4. The interlocking cannula system of claim 1, wherein each respective cannula of the plurality of cannulas includes a head including a first side and a second side, and a tube extending from the second side of the head.

5. The interlocking cannula system of claim 4, wherein the head of each of the cannulas is the same size.

6. The interlocking cannula system of claim 4, wherein the respective locking mechanisms of each of the plurality of cannulas are configured such that the tubes of two interlocked cannulas among the plurality of cannulas are concentric with one another.

7. The interlocking cannula system of claim 4, wherein the head of each of the cannulas includes the respective locking mechanism.

8. An interlocking cannula system comprising:
a plurality of cannulas comprising a first cannula, a second cannula, and a third cannula, wherein the first cannula is smaller than the second cannula and the third cannula, and the second cannula is smaller than the third cannula, thereby allowing the first cannula to be nested within the second cannula and/or the third cannula,
wherein each of the plurality of cannulas includes a respective locking mechanism, which allows the first cannula to be interlocked with the third cannula without the second cannula therebetween and which allows the second cannula to be interlocked with the third cannula,
wherein each of the respective locking mechanisms includes a female locking component and a male locking component,
wherein each respective cannula of the plurality of cannulas includes a head including a first side and a second side, and a tube extending from the second side of the head, and
wherein the head includes the female locking component on the first side and the male locking component on the second side.

9. The interlocking cannula system of claim 8, wherein the male locking components of each of the plurality of cannulas are substantially identical.

10. The interlocking cannula system of claim 8, wherein the female locking components of each of the plurality of cannulas are substantially identical.

11. The interlocking cannula system of claim 8, wherein a cross-sectional shape of the male locking component comprises two straight sides and two curved sides.

12. The interlocking cannula system of claim 8, wherein the male locking component comprises an extension, wherein the female locking component comprises a notch configured to receive the extension, and wherein the notch comprises a circular cross-section which allows the extension to rotate about an axis when received in the notch.

13. The interlocking cannula system of claim 8, wherein the male locking component comprises an extension, wherein the female locking component comprises a notch configured to receive the extension, and wherein the notch comprises a rectangular cross-section.

14. An interlocking cannula system comprising:
a plurality of cannulas comprising a first cannula, a second cannula, and a third cannula, wherein the first cannula is smaller than the second cannula and the third cannula, and the second cannula is smaller than the third cannula, thereby allowing the first cannula to be nested within the second cannula and/or the third cannula,
wherein each of the plurality of cannulas includes a respective locking mechanism, which allows the first cannula to be interlocked with the third cannula without the second cannula therebetween and which allows the second cannula to be interlocked with the third cannula,
wherein the respective locking mechanisms are configured such that interlocking one cannula of the plurality of cannulas with another cannula of the plurality of cannulas includes compressing the one cannula inward.

15. An interlocking cannula system comprising:
a plurality of cannulas comprising a first cannula, a second cannula, and a third cannula, wherein the first cannula is smaller than the second cannula and the third cannula, and the second cannula is smaller than the third cannula, thereby allowing the first cannula to be nested within the second cannula and/or the third cannula,
wherein each of the plurality of cannulas includes a respective locking mechanism, which allows the first cannula to be interlocked with the third cannula without the second cannula therebetween and which allows the second cannula to be interlocked with the third cannula,
wherein the respective locking mechanism of the first cannula includes a first threading and a cam,
wherein the respective locking mechanism of the third cannula includes a third threading and a first female locking component,
wherein the respective locking mechanism of the second cannula includes a second threading and a second female locking component, wherein the second threading is configured to engage the first female locking component thereby interlocking the third cannula and the second cannula, and
wherein the first threading is configured to engage the first female locking component thereby interlocking the first cannula and the third cannula, and wherein the cam is configured to engage the second female locking component thereby interlocking the second cannula and the first cannula.

16. The interlocking cannula system of claim 15, wherein the second threading has a larger thread pitch than the third threading.

17. The interlocking cannula system of claim 15, wherein the first female locking component is configured such that the cam cannot engage with the first female locking component.

18. An interlocking cannula system comprising:
a plurality of cannulas comprising a first cannula, a second cannula, and a third cannula, wherein the first cannula is smaller than the second cannula and the third cannula, and the second cannula is smaller than the third cannula, thereby allowing the first cannula to be nested within the second cannula and/or the third cannula,
wherein each of the plurality of cannulas includes a respective locking mechanism, which allows the first cannula to be interlocked with the third cannula without the second cannula therebetween and which allows the second cannula to be interlocked with the third cannula,
wherein the respective locking mechanism of the first cannula includes a first threading and a first coil spring,
wherein the respective locking mechanism of the third cannula includes a third threading and a first female locking component,
wherein the respective locking mechanism of the second cannula includes a second threading, a second coil spring, and a second female locking component,
wherein the second coil spring is configured to engage the first female locking component thereby interlocking the third cannula and the second cannula, and
wherein the first coil spring is configured to engage the first female locking component thereby interlocking the first cannula and the third cannula, and wherein the first coil spring is configured to engage the second female locking component thereby interlocking the second cannula and the first cannula.

19. The interlocking cannula system of claim 18, wherein the second coil spring comprises a greater spring force than the first coil spring.

* * * * *

UNITED STATES PATENT AND TRADEMARK OFFICE
CERTIFICATE OF CORRECTION

| | | |
|---|---|---|
| PATENT NO. | : 12,396,751 B2 | Page 1 of 1 |
| APPLICATION NO. | : 18/531382 | |
| DATED | : August 26, 2025 | |
| INVENTOR(S) | : Jaecker et al. | |

It is certified that error appears in the above-identified patent and that said Letters Patent is hereby corrected as shown below:

In the Specification

Column 13, Line 47, delete "In at least some aspects,"

Signed and Sealed this
Twenty-first Day of October, 2025

John A. Squires
*Director of the United States Patent and Trademark Office*